United States Patent
Li et al.

(10) Patent No.: US 7,537,605 B2
(45) Date of Patent: *May 26, 2009

(54) MEDICAL DEVICE FOR TREATING SKIN ITCH AND RASH

(76) Inventors: Huan-Chen Li, 4 Swedes Crossing, Westford, MA (US) 01886; Xiao-Guang Wang, 4 Swedes Crossing, Westford, MA (US) 01886

( * ) Notice: Subject to any disclaimer, the term of this patent is extended or adjusted under 35 U.S.C. 154(b) by 0 days.

This patent is subject to a terminal disclaimer.

(21) Appl. No.: 10/428,253

(22) Filed: May 3, 2003

(65) Prior Publication Data

US 2004/0127962 A1 Jul. 1, 2004

Related U.S. Application Data

(63) Continuation-in-part of application No. 10/165,893, filed on Jun. 10, 2002, now abandoned, which is a continuation-in-part of application No. 09/758,706, filed on Jan. 11, 2001, now Pat. No. 6,635,075, which is a continuation-in-part of application No. 09/502,992, filed on Feb. 11, 2000, now Pat. No. 6,245,093, which is a continuation-in-part of application No. 09/183,639, filed on Oct. 30, 1998, now abandoned, which is a continuation-in-part of application No. 08/698,323, filed on Aug. 14, 1996, now abandoned, which is a continuation-in-part of application No. 08/601,196, filed on Feb. 14, 1996, now abandoned, which is a continuation-in-part of application No. 08/254,273, filed on Jun. 6, 1994, now abandoned, which is a continuation-in-part of application No. 08/157,572, filed on Nov. 24, 1993, now abandoned, which is a continuation-in-part of application No. 08/131,987, filed on Oct. 4, 1993, now abandoned.

(51) Int. Cl.
*A61F 2/00* (2006.01)
*A61F 7/00* (2006.01)
*A61F 7/12* (2006.01)

(52) U.S. Cl. .................................. 607/96; 607/101

(58) Field of Classification Search ............ 607/96–101
See application file for complete search history.

(56) References Cited

U.S. PATENT DOCUMENTS

| | | | |
|---|---|---|---|
| 1,817,823 A | 8/1931 | Ito | |
| 2,440,041 A | 4/1948 | Clark | |
| 3,325,627 A | 6/1967 | Adler et al. | |
| 3,625,202 A | 12/1971 | Oyoshirhara | |
| 3,938,526 A * | 2/1976 | Anderson et al. | 606/189 |
| 3,978,312 A | 8/1976 | Barton et al. | |
| 3,982,542 A | 9/1976 | Ford et al. | |
| 4,074,110 A * | 2/1978 | Slaughter | 219/240 |
| 4,090,517 A * | 5/1978 | Takenaka | 604/114 |
| 4,155,164 A | 5/1979 | White | |
| 4,266,556 A | 5/1981 | Barlow et al. | |
| 4,381,009 A * | 4/1983 | Del Bon | 607/96 |
| 4,449,528 A * | 5/1984 | Auth et al. | 606/31 |
| 4,582,057 A | 4/1986 | Auth et al. | |
| 4,657,531 A * | 4/1987 | Choi | 604/23 |
| 4,691,703 A | 9/1987 | Auth et al. | |
| 4,744,359 A | 5/1988 | Hatta et al. | |
| 4,747,841 A | 5/1988 | Kuratomi et al. | |
| 4,748,979 A * | 6/1988 | Hershenson | 606/28 |
| 4,763,657 A | 8/1988 | Chen et al. | |
| 4,878,493 A | 11/1989 | Pasternak et al. | |
| 4,907,589 A | 3/1990 | Cosman | |
| 4,944,297 A * | 7/1990 | Ratkoff et al. | 607/96 |
| 4,961,422 A | 10/1990 | Marchosky et al. | |
| 5,097,828 A | 3/1992 | Deutsch | |
| 5,107,832 A | 4/1992 | Guibert et al. | |
| 5,169,384 A | 12/1992 | Bosniak et al. | |
| 5,191,883 A | 3/1993 | Lennox et al. | |
| 5,197,466 A | 3/1993 | Marchosky et al. | |
| 5,327,886 A | 7/1994 | Chiu | |
| 5,376,087 A | 12/1994 | Haber et al. | |
| 5,445,146 A | 8/1995 | Bellinger | |
| 5,456,682 A * | 10/1995 | Edwards et al. | 606/31 |
| 5,459,298 A * | 10/1995 | Tschakaloff | 219/227 |
| 5,524,809 A * | 6/1996 | Kosslow et al. | 228/20.5 |
| 5,540,679 A | 7/1996 | Fram et al. | |
| 5,591,219 A | 1/1997 | Dungan | |
| 5,658,583 A | 8/1997 | Zhang et al. | |
| 5,662,624 A | 9/1997 | Sundstrom et al. | |
| 5,688,266 A | 11/1997 | Edwards et al. | |
| 5,830,211 A | 11/1998 | Santana et al. | |
| 6,066,164 A | 5/2000 | Macher et al. | |
| 6,091,995 A | 7/2000 | Ingle et al. | |

| | | | |
|---|---|---|---|
| 6,102,705 A | 8/2000 | Darnell | |
| 6,134,475 A | 10/2000 | Will | |
| 6,162,217 A | 12/2000 | Kannenberg et al. | |
| 6,235,027 B1 | 5/2001 | Herzon | |
| 6,245,093 B1 * | 6/2001 | Li et al. ................. | 607/96 |
| 6,254,391 B1 | 7/2001 | Darnell | |
| 6,283,931 B1 | 9/2001 | Augustine | |
| 6,293,917 B1 | 9/2001 | Augustine et al. | |
| 6,303,142 B1 | 10/2001 | Zhang et al. | |
| 6,306,431 B1 | 10/2001 | Zhang et al. | |
| 6,322,583 B1 | 11/2001 | Tu et al. | |
| 6,340,301 B2 | 1/2002 | Darnell | |
| 6,340,472 B1 | 1/2002 | Zhang et al. | |
| 6,350,262 B1 | 2/2002 | Ashley | |
| 6,382,979 B2 | 5/2002 | Lindquist | |
| 6,465,006 B1 | 10/2002 | Zhang et al. | |
| 6,465,709 B1 | 10/2002 | Sun et al. | |
| 6,471,716 B1 | 10/2002 | Pecukonis | |
| 6,485,506 B2 | 11/2002 | Augustine | |
| 6,497,575 B2 | 12/2002 | Zavitsanos et al. | |
| 6,533,778 B2 | 3/2003 | Herzon | |
| 6,587,731 B1 | 7/2003 | Ingle et al. | |
| 6,589,270 B2 | 7/2003 | Augustine | |
| 6,613,350 B1 | 9/2003 | Zhang et al. | |
| 6,626,901 B1 | 9/2003 | Treat et al. | |
| 6,629,974 B2 | 10/2003 | Penny et al. | |
| 6,635,075 B2 * | 10/2003 | Li et al. ................. | 607/96 |
| 6,660,029 B2 | 12/2003 | VanSkiver et al. | |
| 6,702,808 B1 | 3/2004 | Kreindel | |
| 6,708,060 B1 | 3/2004 | Avrahami et al. | |
| 6,726,673 B1 | 4/2004 | Zhang et al. | |
| 6,772,013 B1 | 8/2004 | Ingle et al. | |
| 6,780,426 B2 | 8/2004 | Zhang et al. | |
| 6,840,955 B2 | 1/2005 | Ein | |
| 6,860,880 B2 | 3/2005 | Treat et al. | |
| 6,908,463 B2 | 6/2005 | Treat et al. | |
| 7,083,613 B2 | 8/2006 | Treat | |
| 7,108,694 B2 | 9/2006 | Miura et al. | |
| 7,137,979 B2 | 11/2006 | Conrad et al. | |
| 2001/0012608 A1 | 8/2001 | Darnell | |
| 2001/0041886 A1 | 11/2001 | Durkin et al. | |
| 2002/0026133 A1 | 2/2002 | Augustine et al. | |
| 2002/0156471 A1 | 10/2002 | Stern et al. | |
| 2002/0165529 A1 | 11/2002 | Danek | |
| 2003/0023286 A1 | 1/2003 | Augustine et al. | |
| 2003/0125735 A1 | 7/2003 | Herzon | |
| 2003/0199866 A1 | 10/2003 | Stern et al. | |
| 2006/0036194 A1 | 2/2006 | Schultheiss et al. | |

FOREIGN PATENT DOCUMENTS

| | | |
|---|---|---|
| CN | 90225220.8 | 11/1990 |
| CN | 95315109.3 | 8/1995 |
| CN | 94116233 | 12/1995 |
| CN | 94221831 | 1/1996 |
| CN | 01337354.4 | 9/2001 |
| CN | 0530200072.2 | 2/2005 |
| DE | 19752282 | 6/1992 |
| DE | 4331945 | 3/1995 |
| DE | 198 08 851 A1 | 11/1998 |
| EP | 1231875 | 8/2002 |
| FR | 2 689 002 | 10/1993 |
| FR | 2720271 | 5/1994 |
| FR | 2 746 296 | 9/1997 |
| JP | 2-104351 | 4/1990 |
| JP | 5248681 | 9/1993 |
| JP | 10-229995 | 9/1998 |
| WO | WO00/53113 A1 | 9/2000 |
| WO | WO/01/03619 | 1/2001 |
| WO | WO-01/03619 | 1/2001 |
| WO | WO03/061497 | 7/2003 |
| WO | WO03/061498 | 7/2003 |

OTHER PUBLICATIONS

Field, S. B., et al. "The Relationship Between Heating Time and Temperature: Its Relevance to Clinical Hyperthermia," Radiology and Oncology, 1 (1983) 179-186.
Bickford, R.G., "Experiments Relating to the Itch Sensation, Its Peripheral Mechanism, and Central Pathways" Clinical Science 3:377-386, 1937.
Glover, R. A. et al. "Histamine release from rodent and human mast cells induced by protoporphyrin and ultraviolet light: studies of the mechanism of mast-cell activation in erythropoietic protoporphyria" British Journal of Dermatology (1990) 122, 501-512.
Treatment of Pruritus, Journal of Family Practice, 1987, vol. 25 No. 5, pp. 438.
Lowitt, M. H. MD, et al. "Pruritus" Seminars in Neurology, vol. 12, No. 4, Dec. 1992.
Medical Letter on Drugs and Therapeutics (British Edition), Consumers' Association 1966 vol. 8 No. 13 pp. 50-51.
Medical Letter on Drugs and Therapeutics (British Edition), Consumers' Association 1969 vol. 11 No. 14 pp. 60.
Ward, L., et al. "A comparison of the effects of noxious and innocuous counterstimuli on experimentally induced itch and pain," Pain 64 (1996) 129-138.
Xu and Qian, "Analysis of Thermal Injury Process Based on Enzyme Deactivation Mechanisms," 462, vol. 117, Nov. 1995.
Itch Zapper, Home Health Products, http://www.safehomeproducts.com/SHP/HH/ItchZapper.asp, Aug. 12, 2003.
Sybaritic, Symedex Medical Spa Specialists, "Advanced Pulsed Light System Performs Both Photoepilation & Acne Photoclearance" SpectraClear 2003, 2 pgs.
John C. Chato, "Thermal Therapy of Toe Nail Fungus," International Mechanical Engineering Congress and Exposition, Nov. 11-16, 2000, Orlando, Florida, pp. 1 & 2.
R. A. Glover, et al., "Histamine release from rodent and human mast cells induced by protoporphyrin and ultraviolet light: Studied in the mechanism of mechanism of mast-cell activation in erythropoietic protopophyria," British Journal of Dermatology, 1990, pp. 501-512.

* cited by examiner

*Primary Examiner*—Robert L Nasser
(74) *Attorney, Agent, or Firm*—Mintz, Levin, Cohn, Ferris, Glovsky and Popeo, P.C.

(57) ABSTRACT

An apparatus and method that is effective for the treatment of skin itch and skin rash is disclosed. The apparatus is contained within a body which can be easily manipulated with one hand, and which is powered by a self-contained battery. Also contained within the body is a heating means, controlled by a thermostat, a temperature selector if the heating means if intended to provide multiple temperatures, and means to warn the user when the desired temperature is reached. In addition the apparatus includes means to apply the heat in a cyclical manner, in which the heat is repeatedly applied and removed, with a cycle time and pulse width in which is controlled by user by means of a control located on the body heater and some other elements that can ensure only one substantially unique temperature is used. The method, which is related to the apparatus as its governing principle, includes the application of heat at a precise, controlled temperature, for a specific period of time, t the skin at the location of the itch or rash. The temperature used depends upon the nature of skin discomfort, but is generally inside the range between 46-62° C. The temperature variation is generally controlled within +/−0.5° C. although it can be wider or narrower depends upon the nature of the itch treatment. In addition, the method includes a pulsating application of heat to the skin area, in which the heat is alternately applied and removed at a rate of approximately 1 second, with a total application time of between 10 and 30 seconds.

33 Claims, 8 Drawing Sheets

MEDICAL DEVICE FOR TREATING SKIN ITCH AND RASH

CONTINUING DATA

This application is a continuation-in-part of application Ser. No. 10/165,893 filed on Jun. 10, 2002, abandoned, which is a continuation-in-part of the application Ser. No. 09/758,706 filed on Jan. 11, 2001, now U.S. Pat. No. 6,635,075, which is a continuation in part of application filed on Ser. No. 09/502,992 filed on Feb. 11, 2000, now U.S. Pat. No. 6,245,093, which is a continuation-in part of application Ser. No. 09/183,639 filed on Oct. 30, 1998, now abandoned, which is a continuation in part of application Ser. No. 08/698,323 filed on Aug. 14, 1996, now abandoned, which is a continuation in part of application Ser. No. 08/254,273 filed Jun. 6, 1994, now abandoned, which is a continuation in part of application Ser. No. 08/131,987 filed Oct. 4, 1993, now abandoned, which is a continuation in part of application Ser. No. 08/601,196 filed Feb. 14, 1996, now abandoned, which is a continuation in part of application Ser. No. 08/157,572 filed Nov. 24, 1993, now abandoned, which is a continuation in part of application Ser. No. 08/131,987 filed Oct. 4, 1993 now abandoned.

FIELD OF THE INVENTION

This invention relates to methods and devices for the treatment of inches, rashes, and skin-diseases, and particularly to such methods and devices which effect such treatments by the application of heat at specific temperatures and for specific periods of time.

BACKGROUND OF THE INVENTION

Doctors know that UV light relieves psoriasis and eczema, but how? Use activated vitamin D did not give the same effect. It is now known that UV activates a group of genes called stress-genes, which produce stress proteins. These proteins are responsible for keeping the skin healthy and beautiful, and effectively clear up skin problems. Since UV can also cause DNA damage, skin-cancer and skin aging, it is not the ideal means to activate stress-genes. Many other forms of energy have been found to be not only more powerful than UV in activating stress-genes, but also more effective at clearing up skin problems Since heat is the safest energy, it does not cause DNA damage, or skin-cancer, and it is the most effect one in activate stress genes. Also, since the heat destroys toxins below the surface of the skin and shows the best results in clearing up skin-problems, the present invention is intended for the treatment of skin itch, skin rash, and related skin diseases by means of the controlled application of heat.

The use heat in the treatment of skin diseases has been known for a long time folk remedies using heat exist in many different cultures, and the origins of these remedies are often obscure.

However, the use of heat in the treatment of skin itch and rash is different from such treatment for other skin problems. An article in the British Journal of Dermatology 122(4):501-12, 1990, by Benee A. Glover, Cynthia S. Bailey, Kim E. Barrett, S. I. Wasserman and Irma Gifli, of the Division of Dermatology and Allergy Department of Medicine, University of CA, San Diego School of Medicine, San Diego, Calif. entitled: *Histamine release from rodent and human mast cells induced by protoporphyrin and ultraviolet light: studies of the mechanism of mast—cell activation in erythropoietic protoporphyria.*, deals with just this issue. In a study reported therein, it was found that heating or prolonged heating at temperatures lower than 45° C. exacerbates skin itch and rash, but does not have any detrimental effect on most other skin problems. Those temperature ranges found effective against itch and rash are generally in excess of 49° C., Sufficiently hot to result in pain if applied to the skin for more than 3 seconds.

Furthermore, for treating itch and rash the temperature must be maintained at the superficial surface, that is not deeper than dermis where the mast cells are located. This must be done without burning the skin, or causing excessive discomfort. The mast cells must be inactivated, but the inner part tissues such as blood vessels must be maintained at a safe temperature, thus avoiding edema and pain. This is so whether or not the inactivation of mast cells is the sole mechanism for stopping itch. There is some variation of the best effective temperature for treating itch and rash, depending on factors which are discussed below.

The inventor has been found that different types of itches and rashes require different treatment temperatures. These best effective temperatures depend, inter alia, on whether the patient being treated is a child or an adult and women or men, etc. All of the treatment temperatures require, however, are within a range of about 10° C. It has been found that the use of these best effective temperatures, to within a tolerance of plus or minus one-half, effectively avoids side effects, such as edema and rebound of itch. And, for some adults, temperatures below 49° C. should be avoid, as they worsen itch and rash, rather than providing relief. For some toddlers, temperatures above 49° C. should be avoid, as they are too hot. These toddlers will not allow you to apply such a heat, in the case of a metal heater, for a enough time, such as for at least 1-2 seconds, that is required for heat the dermis to the effective temperature, therefore, mast cells cannot be inactivated and the itch will be worsen. Temperatures around 49+/−0.5° C. have been fond optimum for most children, as have temperatures of 51.5+/−0.8° C. for adults and 47+/−0.5° C. is for toddlers and some temperature sensitive women, in the case of itch. The temperature needs better control for temperature sensitive people and areas than for normal people. A variation of +/−0.25° C. or even narrower may be better for them.

Different parts of the body have also been found to have different best effective temperatures. For example, 50° C. is the best temperature for a child or an adult face, 52° C. for adult body and arm skin, and 54° C. for adult leg skin. If 50° C. is used for adult leg skin that is thicker than the face skin, the itch will not be stopped and side effects, such as edema and rebound of itch, may result. Furthermore, best effective temperature is also dependent upon the rate at which the skin is heated, and for that reason best effective temperature may change with changed in the material actually in contact with the skin. The above temperatures are for a planar steel heating surface, with a 9 volts and 350 mA power supply. Different power supplies may also cause the best effective temperatures to change.

New versions of the device are in development which will allow regulation of the temperature to take into account personal variations of the best effective temperature.

Experimental results, as well as the report of Glover, et al., Id., make it clear that the heating time of the skin should be as short as possible, while still receiving the benefit required. Thus the direct contact of the heating element to the skin provides the most direct method to effect an optimum treatment of this nature. This direct contact is accomplished in the present invention by a circular metal heat transfer surface of approximately one inch diameter. The direct contact also provides advantage in controlling the speed to heat up the skin some materials can control the amount of heat to pass to the skin in a timely manner. They will be used as the skin heater or be put on the surface of the skin-heater so to heat the skin to the desired temperature in an desired time. This will avoid the pain and effectively clear up the itch. The reason for this is because if the skin is heated up to fast, it will get pain, if too slow, it will worsen the itch.

At present, there exist a number of commercially available heating pads that apply heat to the skin for therapeutic purposes. However, none of these is effective against skin itch and rash, because none of them accurately and precisely apply the required temperatures for treating itch and rash. These heating pads are intended to heat a large area of the body for more than 20 minutes. They have to provide temperatures not significantly higher than 43° C., otherwise, they will cause burning. There are also commercially available devices like our Electronic Itch Stopper which is available at http://www.ItchStopper.com. They are all covered by our prior applications before they came on the market.

Other apparatuses that are already known to heat the skin for therapeutic purposes are as described, for example, in the documents of U.S. Pat. No. 4,763,657 (Chen); U.S. Pat. No. 4,657,531 (choi); and U.S. Pat. No. 4,907,589 (Cosman). None of these have provisions to precisely control and maintain temperature, as required of the current invention. It is so obvious that U.S. Pat. No. 4,090,517 (Takenaka) cannot provide a specific and a narrowed temperature, which is essential for skin itching problems and required of the current invention.

Other old methods of heat treatment for skin ailments include the use of scalding water to heat the skin to stop itch. This method obviously can not be done with the amount of control required to effect the best effective temperature, or with control of the time of application. For these reasons, this method has been abandoned.

Our invention has shown great success both in our clinical trials and in practical use by consumers in the treatment of insect bites, psoriasis, eczema, acne, hives, poison ivy/oak, dermatitis, allergic skin itching, renal failure skin itching, hepatitic skin itching, and all other skin itches. It erases the itch in seconds and clear acute and chronic skin problems quickly.

The apparatus disclosed in detail below is both practical and economical to use. In addition to its preferred forms it may be made in a variety of sizes and shapes.

The device includes easy-to-understanding instructions which specify the best effective temperature for a variety of skin conditions, skin types, and ages. A light indicator located on the body of the invention flashes when the heater reaches the predetermined temperature commanded by the temperature selector, and the user is instructed not to apply the heater until this indicator flashes. In alternate embodiments, a sonic signal is used t indicate that the devices has reached its operating temperature.

A further alternative embodiment includes a heating surface which repetitively retracts and extends. This automatic intermittent application of the heater is especially important when higher temperatures are required for the treatment, since higher temperature require shorter application times, repeated at short intervals.

Because the effective temperature against itch can be so high as to be intolerable if applied for longer than 3 seconds, means are provided to heat the skin to the effective temperature range, such as 52° C., for about 2 seconds and then let it cool down to a tolerable temperature, such as 47° C., for about half second. This process is repeated for between one to ten minutes in order to cure skin diseases.

SUMMARY OF THE INVENTION

The invention is to make an heating apparatus work on skin itching and problems. Our apparatus has two unique features. First, the apparatus can provide a specific temperature such as 50° C. Second the temperatures is substantially unique which means its variation is so narrow as to work for a unique case. It is a further object of this invention to provide such an apparatus which is simple, inexpensive, and portable.

An array of apparatus each comprises heating means providing one single predetermined specific temperature inside the range of about 46 to 62° C., the heating means are capable of raising the skin to the temperature within a desired time such as within 10 seconds or 20 seconds, and maintaining it at that temperature, control means to control the heating means temperature within +/− about 2° C., 1° C., 0.5° C. or even 0.25° C. depend on specific treatments, a power source means to provide enough energy for the heating means. All of these are contained within a housing comprising a contact end, with the heating means positioned in the contact end. Each kind of apparatus in this array will provide a substantially unique temperature for a specific treatment, such as one provides 47+/−0.5° C. for children and another provides 51+/−0.8° C. for adults.

A more complicated one, in addition to the above means, comprises temperature selection means within the range of 46 to 62° C. The above heating means can provide any single temperature in 46 to 62° C. The selection means is also contained within the housing and are accessible to the user.

According to a second aspect of the invention, the apparatus further comprises a substantially planar heat transfer surface located at the contact end, heated by said heating means. This surface is substantially circular, with a diameter of at least one-half inch. Material that allow a desired amount of heat to pass to the skin in a desired time may be used as the planar or be put on the surface of it.

According to a third aspect of the invention, the apparatus further comprises signaling means to indicate that the user's skin is at the selected temperature, as well as means to select one of a multiplicity of temperatures, each such temperature comprising a best effective temperature for a particular treatment, and comprising means to control skin temperature to within one-half degree centigrade.

According to a forth aspect of the invention, the heating means further comprises a slideably moveable heating surface positioned within the contact end, said heating surface having an extended position in which the surface is in contact with the skin of the user and a retracted position out of contact with the skin. Also included are means to position the surface at either position, and selection means to control said motion.

According to a fifth aspect of the invention, the positioning and selection means provide a periodic motion of the heating surface, and the selection means provides control of frequency and duty cycle of said motion.

According to a sixth aspect of the invention, the apparatus further comprises means to select one or more additional temperatures, so that, when cyclical operation is selected, heat will be alternately be applied first at the first selected temperature, then at the second selected temperature, and so on until all the selected temperatures have been applied in sequence, then at the selected temperature, and repeating indefinitely.

According to a seventh aspect of the invention, the apparatus further comprises a grid at the contact end, said grip having a multiplicity of apertures. The heat transfer surface contains a multiplicity of protrusions which extend through the grid apertures when the surface is in extended position.

BRIEF DESCRIPTION OF THE DRAWINGS

These, and further features of the invention, may be better understood with reference to the accompanying specification and drawings depicting the preferred embodiment, in which.

PREFERRED EMBODIMENTS

A number of preferred embodiments of the invention are discussed in this section.

Figure 1:
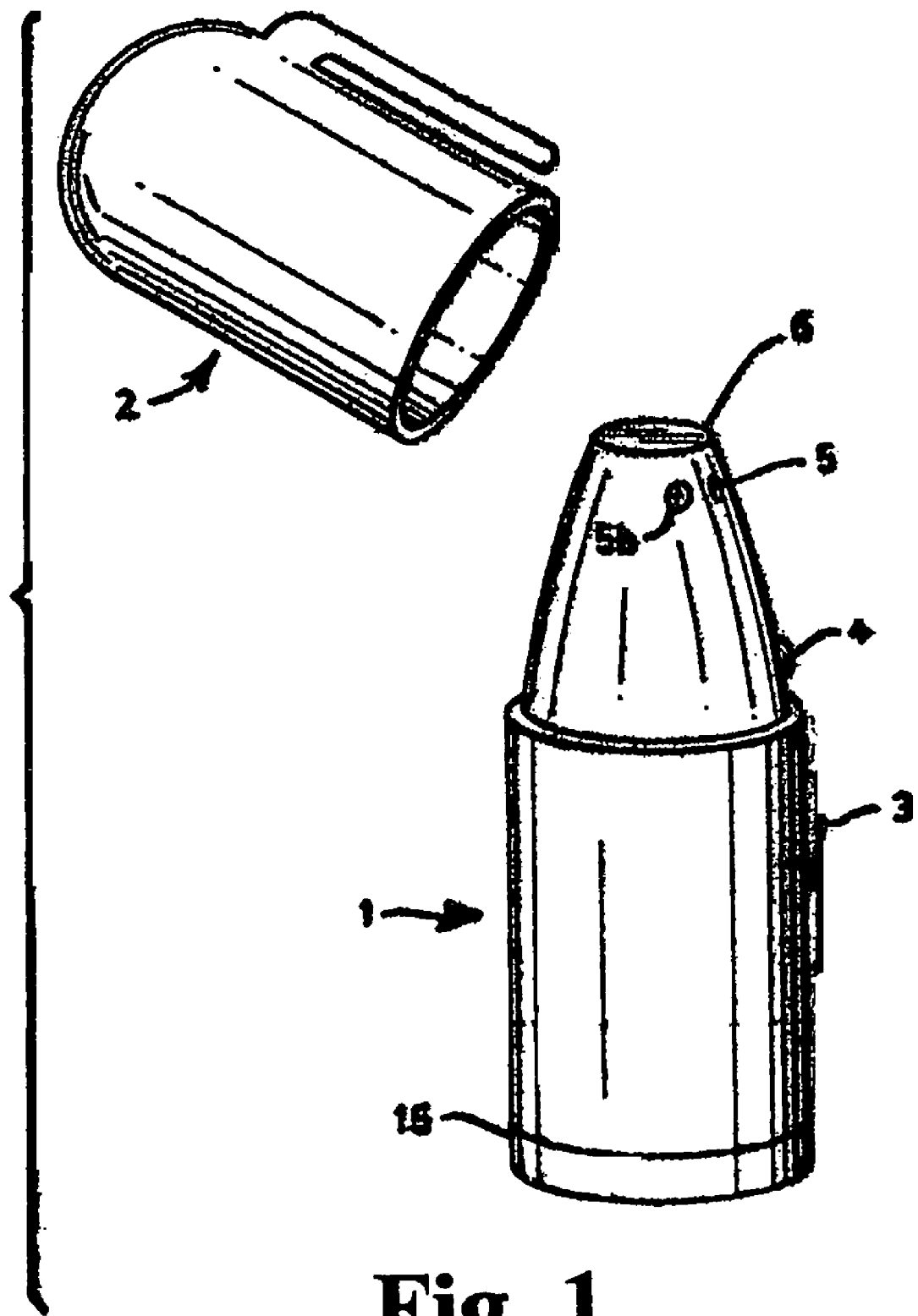
FIG. 1 is a perspective view of the present invention in its first preferred embodiment.

The first preferred embodiment of the apparatus may be understood by referring to FIG. 1, showing the invention is in the form of a hand-held apparatus with self-contained power supply by means of commercially-available batteries. The apparatus includes an optional protective cap 2 and a housing 1 which contains all the remaining components of the invention. A temperature selector 3 is located half-way up the body 1. This selector is of a rotary type which selects the best effective temperature in 1 degree-centigrade increments, to within one-half-degree centigrade. A main power switch 4, turns power on and off. Light indicator 5 illuminates when the selected temperature has been reached, and light indicator 5b illuminates when power is on. Heat is applied to the skin through the heat application surface 6. A temperature transducer, or thermostat 7, is located directly adjacent to the heat application surface, so that the temperature detected is essentially that of the user's skin during application. The batteries which serve as the power source 8 are located within lower portion of the housing. Batteries are replaced by means of a screw-on cap 15, at the bottom end of the housing.

In the case of an array of apparatus, we will remove the above the temperature selector 3 and make each kind of apparatus in the array to provide a single temperature.

The temperature selector 3 is used in such a manner as to enable users to directly select one best effective temperature for the heater. It provides for selection of two or more predetermined temperatures. Different versions of this embodiment are provided for different ranges of temperatures, depending upon general application.

The heat application surface may be made of a number of different materials. A heat conductive metal is one of the preferred materials, especially when used in conjunction with a magnetic-induction type heater, as is the case with the first preferred embodiment. The surface may alternatively be covered by a non-heat-conducting coating, or material, such as a thin layer of rubber, in order to reduce pain by reducing the conduction speed of the heat to the skin. Many users are more comfortable when the temperature rises gradually to the best effective temperature. Such a gradual temperature rise is found to be equally effective as a rapid rise, in regard to the curing of skin itch and rashes.

Figure 1B:
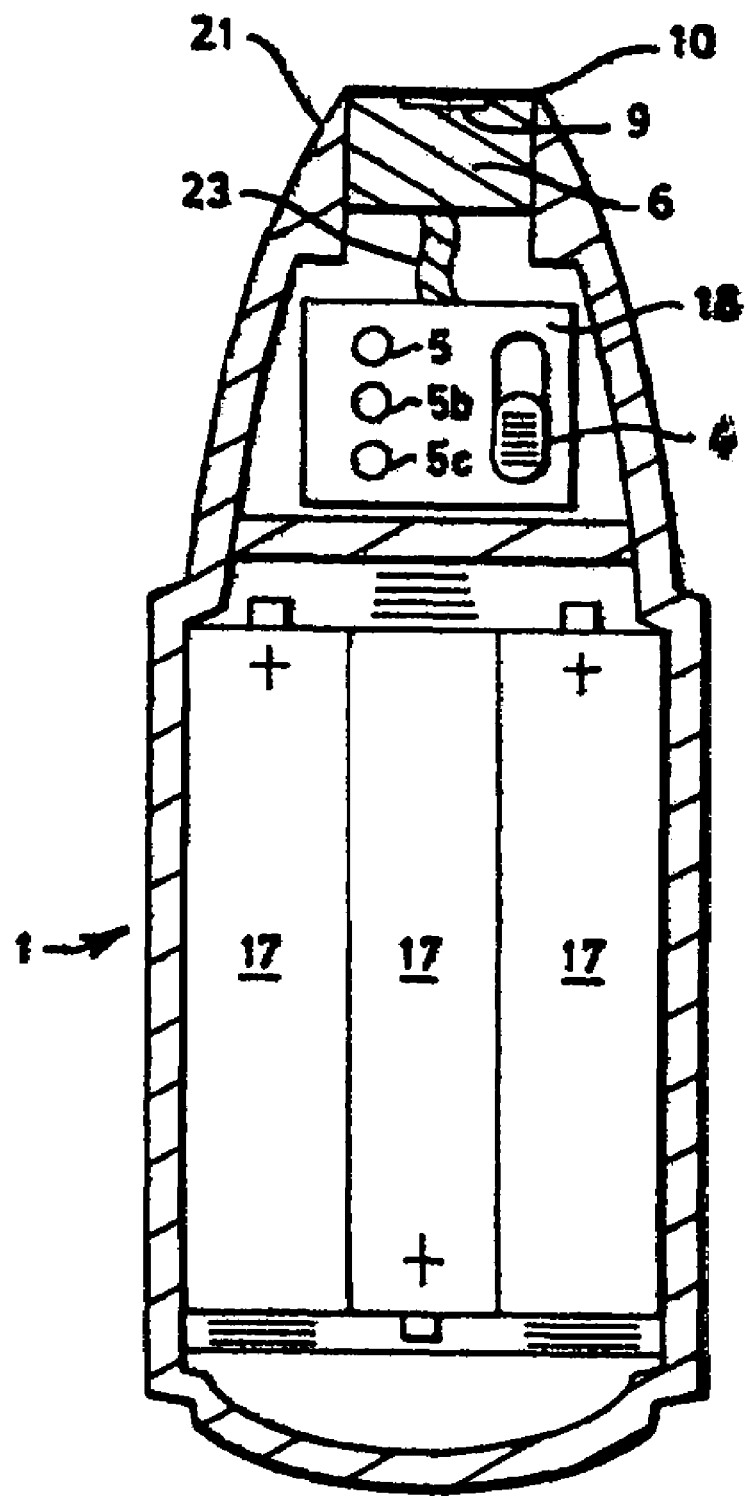
FIG. 1B is a cross-section view of the model SM version of the invention, a variation of the first preferred embodiment.

A variation of the first preferred embodiment is shown as FIG. 1b, and corresponds to a commercially-offered version of this invention, model SM, as mentioned above. In this cross-section view, the batteries are show as the commonly used "AA" cells, with three such cells 17 mounted within the housing 3 as described above. The electronics used to control the device are mounted on circuit board 18, located in the upper part of the housing as shown. In model SM, there is a third indicator light 5c, mounted on the circuit board together with indicator lights 5 and 5b. In this implementation, the indicators represent "Ready"5, "Child 5c", and "Adult"5b. In the implementation of FIG. 1B the switch 4 has three positions, corresponding to off, "Child", and "Adult". The Adult and Child switch positions correspond to two different temperatures, thought to be optimum for eczema and psoriasis, for children and adults, respectively. When either Child or Adult position is selected, the Ready light indicates that the apparatus has reached the selected temperature. In this embodiment, the heat application surface presents a flat, circular surface flush with the contact end of the housing, as shown in FIG. 1a. This surface has a diameter of approximately 3/8 inch.

The heating transfer surface in this embodiment is combined with the heating element itself in one integral unit. The circuit board contains control electronics which supplies current to the heating element through cable 21 when the temperature sensed is below the temperature commanded by temperature selector 3. If the temperature reaches or exceeds the temperature commanded, the current is discontinued. The control electronics provide a smooth response profile(i.e. temperature vs. time), with a minimum of overshoot, to a precision of plus or minus one-half degree centigrade.

A second commercially-available version of this invention, Model LD previously described, is very similar to this first preferred embodiment, except that Model LD has a cord allowing the device to plugged into a normal household utility outlet. The heat transfer surface in this version is metal, and presents a flat, circular plate flush with the contact end, as in Model SM. However, the diameter of the surface in Model LD is approximately one inch. This greater surface area allows application to a larger skin area, and is facilitated by the high power available from using house current as a power source.

Model LD also provides only two indicator lights, indicating "ON/OFF", and "READY". Current version of the Model LD allows 5 temperature selections with the temperature selector.

In one of the variations of this first preferred embodiment, the selector switch allows the user to chose one of many different discrete temperatures within the range of the apparatus. This switch is used in place of the three-position switch of FIG. 1b, and is shown in FIG. 2A. The switch contains a rotor 19, with a pointer 20 to indicate which of the positions is selected. The switch has allowing the selection of one of the temperatures indicated, with one of the positions being "OFF". Only two indicator lights are used in conjunction with this variation: "ON" and "READY". Illumination of the "READY" indicator indicates that the apparatus has reached the selected temperature.

Figure 3:
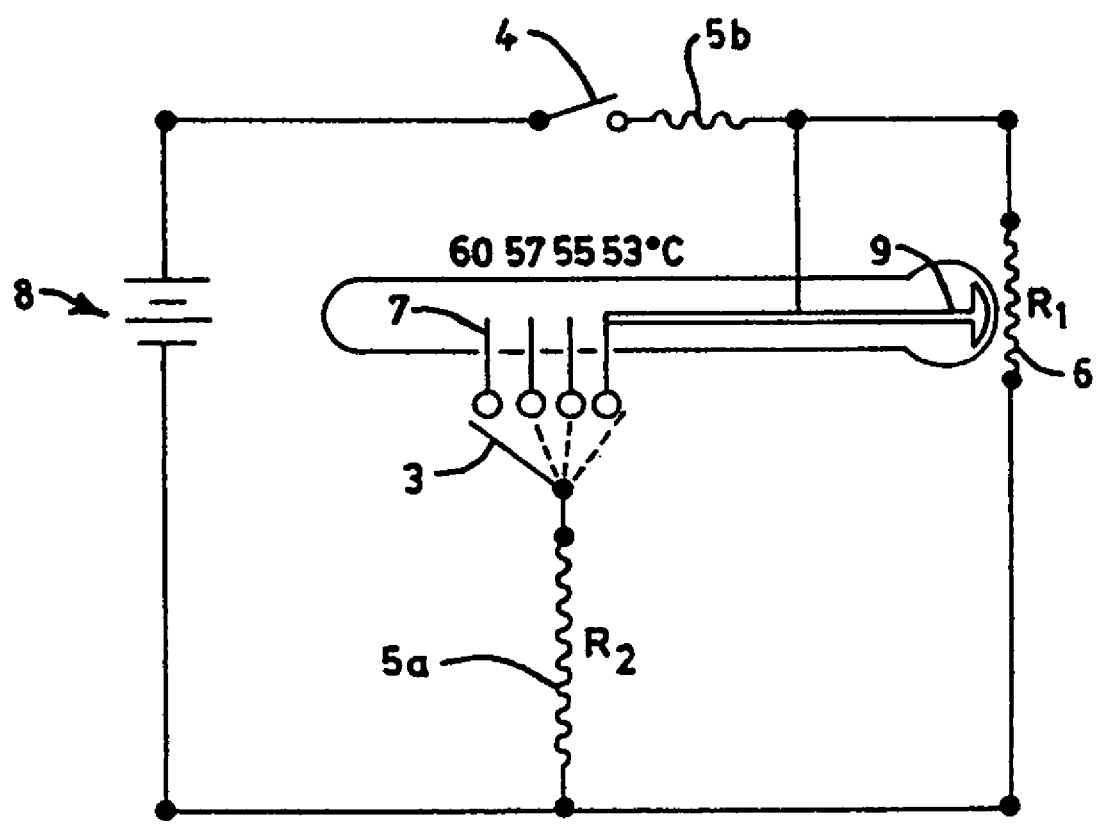
FIG. 3 is a block diagram of he electronic circuit for the temperature probe/thermostat embodiment of the apparatus.

The electronic implementation of the apparatus can take many forms. Many different methods of heating are available, and the art of heat control systems for small appliances is well developed. FIG. 3 depicts the operation of the apparatus in one implementation in the form of an electrical schematic. The power source in the form of a battery 8, is connected through switch 4 in series with indicator light 5b to the temperature transducer 9, and heater 6. The multi-position switch 3 selects one of several contacts which detect different positions along the transducer corresponding to different temperatures. When the selected temperature is reached, the transducer makes an electrical connection with the rest of the system, allowing the "READY" indicator 5a to illuminate. The temperature transducer in FIG. 3 is temperature probe 9 filled with mercury. When the heater is at lower than the selected temperature, the thermostat allows the maximum current to go through the heating element. When the heater reaches the selected temperature, the mercury will serve as a conductor to divide and therefore reduce the heater current, thereby reducing it sufficiently to maintain the selected temperature.

Figure 2:
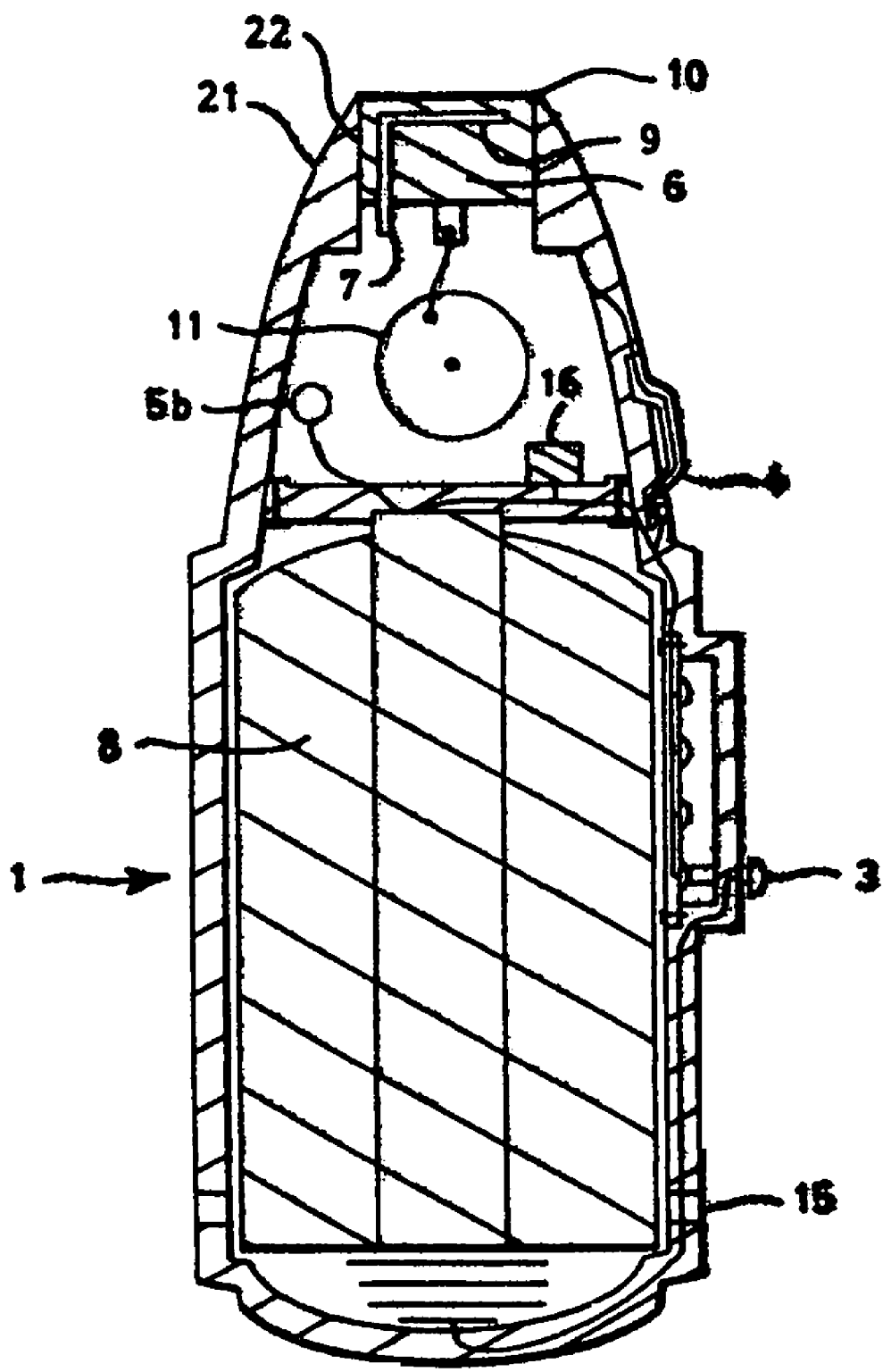
FIG. 2 is a section view of the mechanical pulsation embodiment of the invention.
Figure 2B:
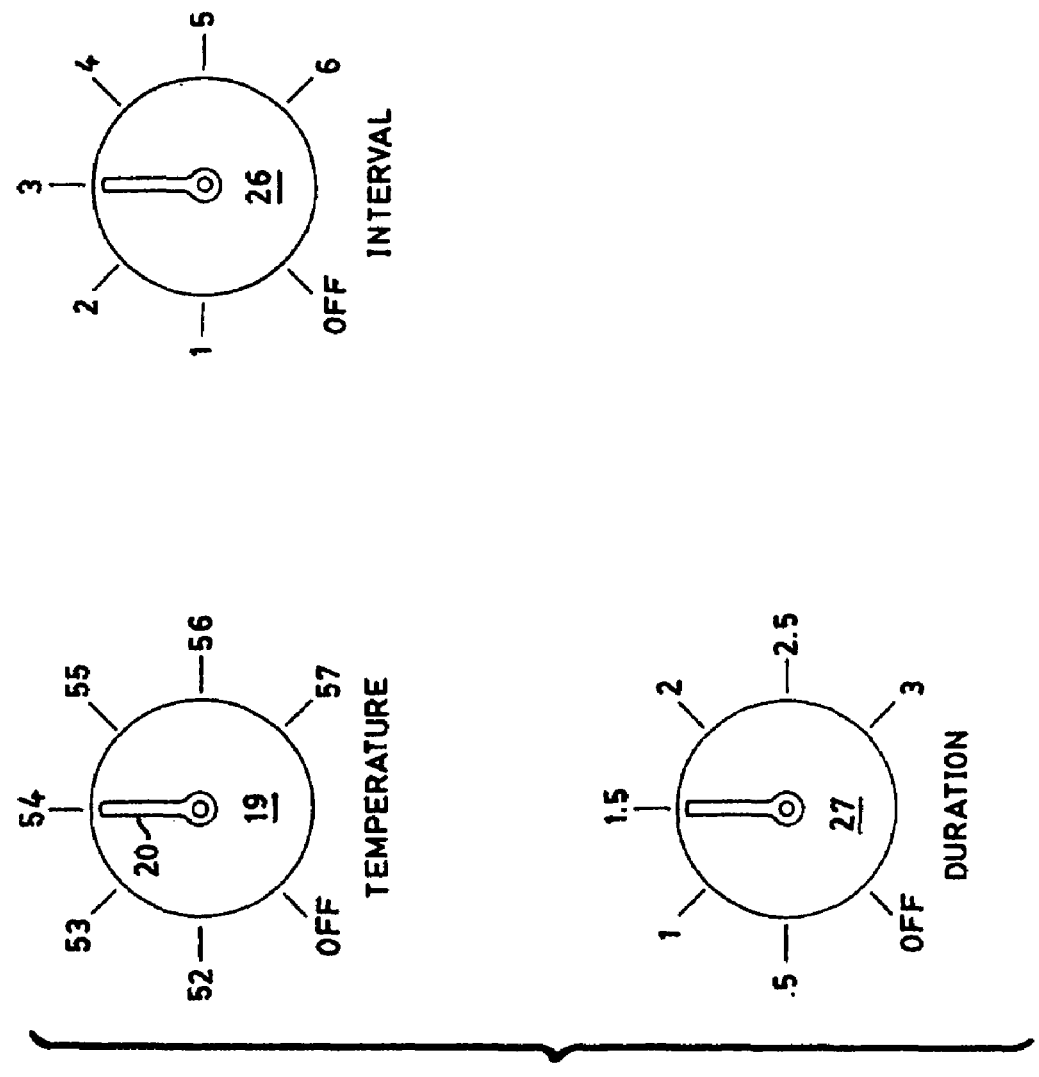
FIG. 2B is a plan view of the selector switches used to control operation of the mechanical pulsation, and indirect heating embodiments.

A second preferred embodiment of the current invention is depicted in FIG. 2. In this embodiment the heat transfer surface/heater combination is slidingly mounted in a channel 22 within the contact end of the apparatus. The heater has an extended position, in which the heater is in contact with the skin of the user, and a retracted position in which the heater is withdrawn within the channel. The heater is driven between its two positions by a positioning mechanism 11, which consists of a motor/crank combination in this embodiment. An alternative variation uses a solenoid as a positioning mechanism in place of the motor/crank actuator.

In this embodiment the temperature selection/detection control moves the heater against the skin of the user, and away from the skin in a repetitive manner, at a rate controlled by the user by means of two selector switches. One such switch controls the rate at which the heater moves against the skin, in seconds per cycle. The second switch controls the duration of the application, in seconds. The ratio of the duration of the application to the time between applications is called the "duty cycle".

It has been found that such a pulsating application of heat is better tolerated by many users than a prolonged application of heat in constant contact with the skin. Toleration varies widely from one individual to another. This embodiment allows users to regulate the duty cycle of the application to suit their individual needs.

A variation of this embodiment includes a grid 10 at the contact end of the apparatus, and in contact with the skin of the user during application. The heat application surface contains raised projections which mate with the grid, and protrude through the grid when the heater is in the extended position, so that these projections are in contact with the skin in this position. This grid provides a safety mechanism when the heating element is retracted. It also allows the temperature detector to be located in the grid itself, which is in contact with the skin, thus providing an more accurate measure of skin temperature.

Figure 4:
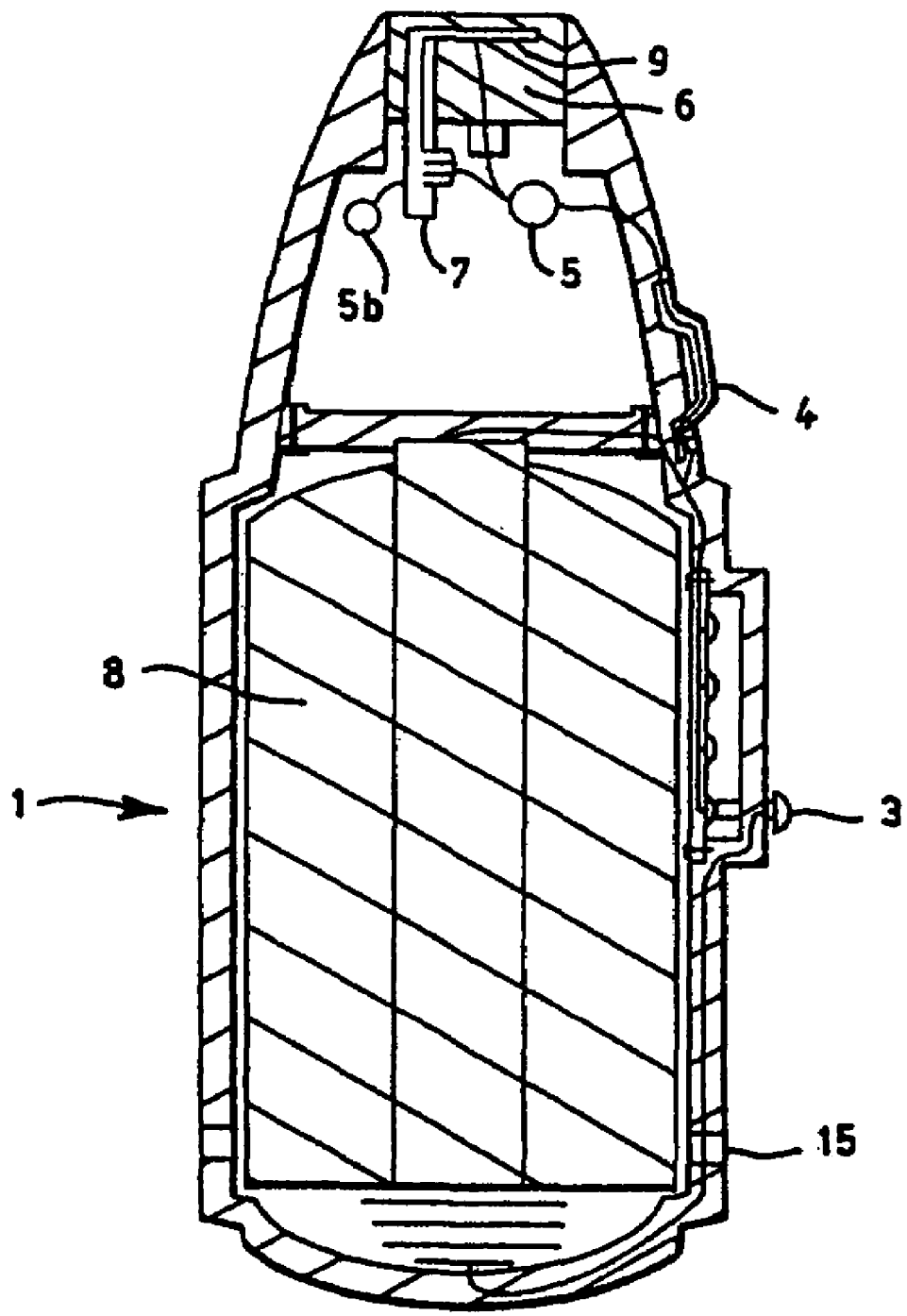
FIG. 4 is a section view of an alternate version of the temperature probe/thermostat embodiment, with alternative location of the thermostat.

The third embodiment as shown in FIG. 4 that omits the positioning means 11 and the grid 10 of the above mentioned embodiment. In this case, a light indicator 5 that will be turned on or will flash or will change color after the heater reaches the selected temperature will be include in this apparatus to replace the omitted elements 10 and 11 to ensure only said best effective temperature is used. Also in this case said heater is fixed at said contact end and said intermittent application of heat is performed manually it would be possible to omit the light indicator 5 if a strong and stable power source, together with a good heat-transfer material for the heat transfer surface are used, providing rapid heating of the transfer surface to the desired temperature, and maintaining of that temperature.

The fourth embodiment as omits the temperature selector of the second embodiment. In this embodiment the heater is fixed at one exact best effective temperature, selected for a specific skin condition.

Figure 5:
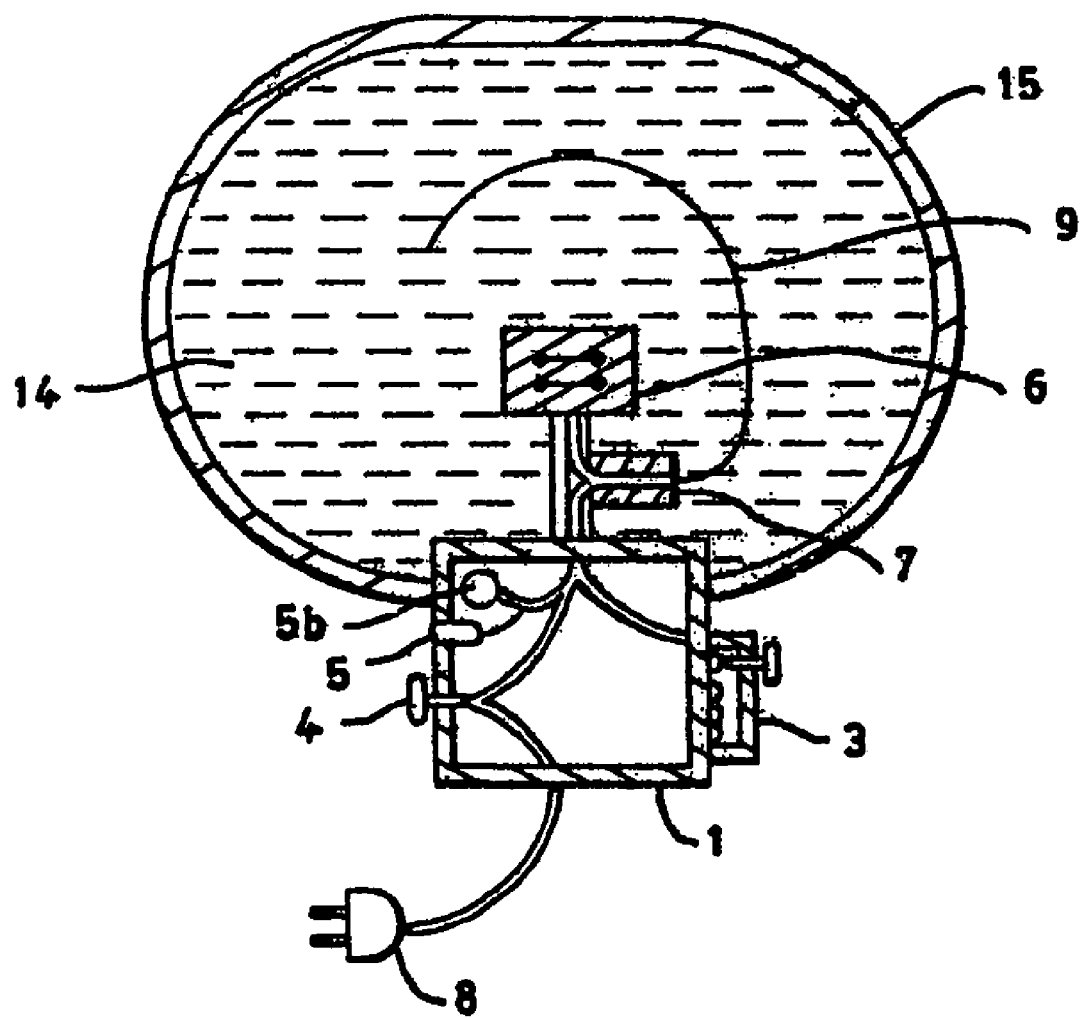
FIG. 5 is a section view of the liquid-filled heating surface embodiment.

In a fifth embodiment, as shown in FIG. 5, a heat-conducting liquid is used to maintain the temperature within the heat transfer surface which contacts the user's skin. The liquid used is preferably one with a high specific heat, such as oils of various types. The material need not be liquid at room temperature, so long as it liquefies at the best effective temperature. The advantage of this method is that the temperature and the sensing device may be located at any point within the liquid, or in proximity to the liquid, simplifying the design and manufacture of the apparatus. The high specific heat of the liquid, as well as the mobility of the molecules within the liquid, produces a uniform temperature within the body of the liquid. In contrast, metals may exhibit a thermal gradient between the area in proximity with the heater and the area in proximity with the skin, making accurate temperature control more difficult. Referring to FIG. 5, the heating element 6 is immersed in the heat transfer liquid 14, while temperature is sensed by the transducer 9, also immersed within the liquid. The liquid is contained within the heater head 25. which may be flexible or semi-rigid. A flexible material provides the advantages of allowing application of heat to a non-planar area of the skin, such as the shoulder or face. The heater head may be made of any material, such as plastic or rubber, which is soft to the touch and does not abrade the skin the head is of a generally spherical, or ellipsoidal shape.

Still referring to FIG. 5, the remainder of this embodiment is similar to the first preferred embodiment. An external power source is used, as indicated by the utility plug 28. Indicator lights 5 and 5b are used to indicate power on, and "READY", as in previous embodiments. A multi-position selector switch 3 is used to select one of several best effective temperatures. Because of the use of an external power source, the heat transfer surface may be significantly larger than in the embodiments powered by self-contained batteries.

Figure 6:
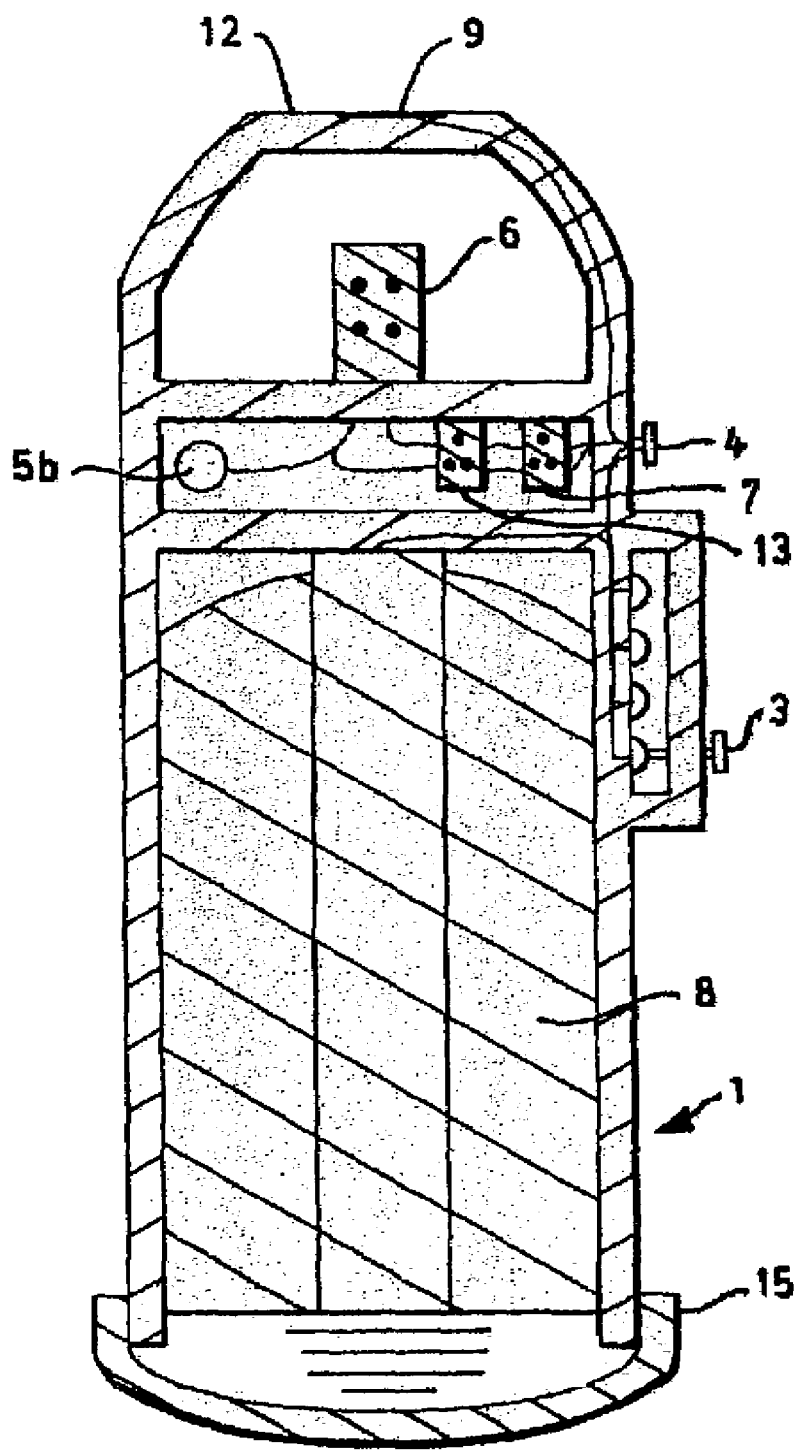
FIG. 6 is a section view of the indirect heating element embodiment.

In a sixth embodiment, as shown in FIG. 6, laser, microwave, sonic sound, and infrared radiation may also be used as a heat source for this invention. Such indirect heat sources require special means to detect heat at the surface of the skin. One recommended method is to incorporate the temperature transducer in a grid 10 located at the contact end of the apparatus, as shown in FIG. 6, which depicts a sixth preferred embodiment of the invention. In this case, the heater source will be set behind the opening at the contact end. The heater should provide a heating energy that is high enough to heat the skin to an effective temperature within about 1-2 seconds. A wall means, such as a grid, is located at this opening to prevent direct contact of the skin to the heat source 6, as will as to prevent the user from accidentally placing his fingers, or other objects, in contact with the heat source burning. In this embodiment, the temperature transducer should be located within the wall means, in order to accurately measure the temperature at the skin of the user.

This embodiment further provides intermittent heating means without requiring a position control mechanism. Intermittent application of the heat to the skin by this method is done by switching the heat source on and off, an alternative method to that of the second preferred embodiment, which uses motor-crank mechanism, or solenoid to physically move the heat transfer surface against the skin, and periodically retract the surface. In the seventh embodiment, the apparatus includes a selector switch allowing the user to vary the duty cycle of the heat application, similar to that of the second preferred embodiment. The temperature transducer located in the wall means senses the temperature at the surface of the skin, and controls heat source so that the skin temperature reaches the temperature commanded by the temperature selector switch 3 at the times commanded by the duty cycle selectors.

A further variation of the invention involves a two chambered pouch that contains one chemical solution in one chamber and another solution in the second chamber. Upon application of pressure through twisting or pressing, the solutions will mix within a third chamber, located within the contact end, thereby heating the surface of the contact end. In another embodiment two chemical solutions would be kept separately in a bottle. Upon spraying or pouring the solution onto the skin the chemical solutions get mixed, resulting in a chemical reaction that provides heat before reaching the skin surface. Strength of the solution would be predetermined such as to provide a specific temperature of a specific range of temperature in 46 C-62° C. The duration of heat is controlled by including in the solution alcohol or a similar chemical that will rapidly cool the surface within a brief predetermined time period. The end result is that the skin is rapidly heated to a temperature and then rapidly cooled.

An additional embodiment requires the use of a single chemical solution, located within an application vessel, to which a catalyst is added just prior to application. The catalyst may be positioned in a spray or pouring spout of the application vessel, such that the chemical solution must pass through the catalyst when the solution is either sprayed or poured. Upon spraying or pouring, the chemical solution in combination with the catalyst is mixed with oxygen in the atmosphere and a chemical reaction occurs providing heat at the skin surface. Still another embodiment would require the use of an electrical heater to heat a medical solution, volatile liquid, or gas to a specific temperature of a specific range of temperature in the range of 46-62° C., 49-62° C. or 50-69° C. The liquid may also become steam or gas in this temperature. The heated spray, heated medical solution, heated steam, or gas, is sprayed onto the skin either continuously or intermittently by manual or automatic operation. The head of the sprayer may be made small and long enough to facilitate the application of the heated spray onto the membrane inside the nose for treating itch within the nose. Thermostatic means for controlling the temperature of the spray or the liquid temperature are included in the sprayer.

The improvement method comprising heating a body heater as may be required to maintain said body heater at a substantially consistent temperature at and during the time of treatment of the skin area affected, said substantially uniform temperature being a predetermined temperature or a predetermined temperature range in ranges of about 49-69° C., 52-62° C., 52-69° C., 53-62° C., 50-62° C., 49-53° C., 54-56° C., 57-62° C., 50-70° C., or 56-62° C., and equal to a best effective temperature of a specific case; continually monitoring the temperature of the body heater to determine when and the degree of heat to be added to the body heater and to determine when adding of heat is to be discontinued; controlling the supply of power to the body heater in accordance with heat requirements determined by said temperature monitoring, and applying the body heater to the skin area that need treatment either continuously or discontinuously. Continually monitoring the temperature of the body heater within about +/−0.5° C. or +/−1° C. of said predetermined temperature, providing of selections of temperature, and indicating readiness to use will be included and these will help to eliminate edema and rebound of itch. The body heater can be dry and wet, such as a wet ribbon heater or a wet towel heater.

Another improvement method comprising using a body heater to heat an skin area as may be required to maintain said skin area at a substantially constant temperature at and during the time of treating said skin area affected, said substantially uniform temperature being a predetermined temperature or a narrow range of temperature in ranges of about 49-69° C., 52-62° C., 52-69° C., 53-62° C., 50-62° C., 49-53° C., 54-56° C., 57-62° C., 50-70° C., or 56-62° C., and equal to a best effective temperature of a specific case; continually monitoring the temperature of the skin area to determine when and the degree of heat to be added to the skin area and to determine when adding of heat is to be discontinued; and controlling the supply of heating power to the skin area in accordance with heat requirements either manually or automatically, or determined by said temperature monitoring. Continually monitoring the temperature of the skin area within about +/−1° C. of said predetermined temperature will help to eliminate edema and rebound of itch. Heating the skin area discontinuously as monitored by a controlling means to heat the skin area to a specific narrow range of temperature in the above ranges and let the skin area to cool down to a tolerable temperature, repeating the heating and cooling until finishing the treatment, to avoid and minimizing any discomfort of heating the skin. The body heater can be dry and wet, such as a wet ribbon heater or a wet towel heater.

It will be apparent tat improvements and modifications may be made within the purview of the invention without departing from the scope of the invention defined in the appended claims.

We claim:

1. A system comprising a plurality of apparatuses, each apparatus comprising:
    a heater adapted to heat a skin area to thereby treat a specific skin condition afflicting the skin area;
    a temperature controller that regulates the heater to a single unalterable temperature upon activation of the apparatus, the single unalterable temperature effectively treating the specific skin condition, the temperature controller maintaining the heater at the single unalterable temperature after the heater reaches the single unalterable temperature which is inside a range of about 46-62° Celsius, each one of the plurality of apparatuses providing a different single unalterable temperature and being labeled to indicate a treatment option for which the one apparatus is to be used;
    a power source providing energy to operate the heater; and
    a housing having a contact end, the heater positioned within the contact end, the temperature controller located within the housing, and the power source means connected to or in the housing.

2. The system as in claim 1, wherein each apparatus further comprises signaling means to indicate that the heater has reached the single unalterable temperature.

3. The system as in claim 1, wherein each apparatus further comprises a heater application surface disposed at the contact end for directly contacting a patient's skin while being heated by the heater; and a temperature sensor disposed proximate the skin contact surface to provide feedback to the temperature controller to maintain the heater application surface at the single unalterable temperature within a tolerance of about +/−1° Celsius, to effectively treat the skin condition.

4. The system as in claim 1, wherein the specific skin condition comprises a skin itch and disease selected from the group consisting of acne, rash, eczema, psoriasis, dermatitis, allergic skin itching, renal failure skin itching, hepatic skin itching, herpes, and systemic skin itch.

5. The system as in claim 1, wherein the specific skin condition comprises a skin itch and disease selected from the group consisting of hives, poison ivy, poison oak, and insect bites.

6. The system as in claim 1, wherein each apparatus further comprises means to control skin temperature to within a tolerance of about +/−1° Celsius after the single unalterable temperature is reached, and for a time sufficient to treat the skin condition.

7. A system as in claim 1, wherein the selected effective temperature of at least one of the apparatuses is within a range of 49 to 53° C.

8. An apparatus for treating skin itch and disease, through the controlled application of heat, comprising:
- a heater for applying heat to skin to treat a specific skin condition;
- a temperature controller for regulation of a heater temperature at a temperature selected to effectively treat the specific skin condition;
- power source means to provide enough energy to operate the heater; and
- a housing having a contact end, the heater positioned within the contact end, the temperature controller located within the housing and the power source means connected to or in the housing,
- wherein the heater further comprises a slideably moveable heating surface positioned within the contact end, the heating surface having an extended position in which the heating surface is in contact with the skin of and a retracted position out of contact with the skin, further comprising means to position the surface at either position; and selection means to control motion of the heating surface.

9. The apparatus as in claim 8, wherein the positioning and selection means provide a periodic motion of the heating surface, and wherein the selection means provides control of a frequency and a duty cycle of the motion of the heating surface.

10. The apparatus as in claim 9, further comprising signaling means to inform a user that the heater is at the selected temperature.

11. The apparatus as in claim 10, further comprising means to select one or more additional temperatures, so that, when cyclical operation is selected, heat will be alternately be applied first at the first selected temperature, then at the second selected temperature, and so on until all the selected temperatures have been applied in sequence, then at first selected temperature, and repeating indefinitely.

12. The apparatus as in claim 11, further comprising a grid at the contact end, said grid having a multiplicity of apertures, whereby the heat transfer surface contains a multiplicity of protrusions which extend through the grid apertures when the surface is in extended position.

13. An apparatus as in claim 8 wherein the temperature selected to effectively treat the specific skin condition is in a range of about 46-62° Celsius.

14. An apparatus for treating skin itch and disease, through the controlled application of heat, comprising;
a) heating means for applying heat to the skin;
b) temperature selection means for allowing selection of a heater temperature that is effective to treat a specific skin condition;
c) power source means to provide enough energy;
d) a housing having a contact end, the heating means positioned within the contact end, the temperature selection means located within the housing, and the power source means connected to or in the housing; and
e) a slideably moveable heating surface positioned within the contact end, said heating surface having an extended position in which the surface is in contact with the skin of the user and a retracted position out of contact with the skin, further comprising means to position the surface at either position; and selection means to control said motion, wherein said positioning and selection means provide a periodic motion of the heating surface, and wherein the selection means provides control of frequency and duty cycle of said motion.

15. The apparatus as in claim 14, further comprising signaling means to inform the user that the heating means is at the selected temperature.

16. The apparatus as in claim 15, further comprising means to select one or more additional temperatures, so that when cyclical operation is selected, heat will be alternately be applied first at the first selected temperature, then at the second selected temperature, and so on until all the selected temperatures have been applied in sequence, then at first selected temperature, and repeating indefinitely.

17. The apparatus as in claim 16, further comprising grid at the contact end, said grid having a multiplicity of apertures, whereby the heater application surface contains a multiplicity of protrusions which extend through the grid apertures when the surface is in extended position.

18. An apparatus as in claim 14 wherein the temperature selected to effectively treat the specific skin condition is in a range of about 46-62° Celsius.

19. A method comprising:
applying a heat application surface of an apparatus to a skin area having a specific skin problem, the apparatus comprising a heating element controlled by a control system that regulates the temperature of the heat application surface to a single unalterable temperature upon activation of the apparatus, the single unalterable temperature effectively treating the specific skin problem, the temperature controller maintaining the heater at the single unalterable temperature after the heater reaches the single unalterable temperature that is in a range of 46° to 62° C.; and
introducing a therapeutically effective quantity of heat energy via the heat application surface, such that the skin area in contact with the heat application surface is raised to, and maintained at, a temperature effective to treat the specific skin problem.

20. The method as in claim 19, further comprising monitoring a skin temperature of the skin area and controlling delivery of heat energy to the skin surface to maintain the skin area at the therapeutic temperature.

21. The method as in claim 19, wherein a manifestation of the skin problem includes a skin lesion.

22. The method as in claim 19, further comprising maintaining the skin area at the predetermined temperature within a tolerance of about +/− one degree Celsius for a period of time sufficient to treat the skin condition.

23. The method as in claim 22, wherein the period of time is greater than 15 seconds.

24. A method as in claim 19 further comprising allowing the skin to cool down to a cooled temperature that is lower than the single unalterable temperature; and repeating the heating up and cooling down for one or more cycles to treat the skin problem.

25. A method comprising:
applying a heat application surface of an apparatus to a skin area having a specific skin problem, the skin problem being selected from acne, rash, eczema, psoriasis, hives poison ivy, poison oak, dermatitis, herpes, and systemic skin itch, the apparatus comprising a heating element controlled by a control system that regulates the temperature of the heat application surface to a single preset temperature that is in a range of 46° to 62° C.; and introducing a therapeutically effective quantity of heat energy via the heat application surface, such that the skin area in contact with the heat application surface is raised to, and maintained at, a temperature effective to treat the specific skin problem.

26. An apparatus comprising:

a heater adapted to heat a skin surface to thereby treat a skin condition afflicting the surface;

a selector that presents two or more treatment options that can be chosen by a user, the treatment options being selected from a group consisting of a specific skin condition, an area of the body to be treated, and a type of patient to be treated, each treatment option corresponding to a discrete heater temperature that is in a range of 46 to 62° C.;

a temperature controller in communication with the selector, the temperature controller regulating the heater to the discrete temperature that corresponds to the treatment option chosen by the user;

a power source providing energy to operate the heater; and a housing having a contact end, the heating means positioned within the contact end, the temperature selection means located within the housing, and the power source means connected to or in the housing.

27. The apparatus as in claim 26, wherein the plurality of discrete temperatures presented by the selector are in a range of 49 to 53° Celsius.

28. The apparatus as in claim 26, wherein the temperature controller maintains the heater at the chosen temperature that has been selected by the user within a tolerance of about +/−1° C. after the chosen temperature is reached.

29. The apparatus as in claim 26, wherein the selector allows selection of two discrete temperatures for the heater, both discrete temperatures being within a range of 49-53° Celsius, one discrete temperature being appropriate for treatment of children and the other discrete temperature being appropriate for treatment of adults.

30. The apparatus as in claim 26, wherein the heater is adapted to provide sufficient thermal transfer capacity and to provide sufficient thermal contact with the skin, that, from the time that contact is established between the heater at the discrete temperature that corresponds to the chosen treatment option and the skin area, the skin area temperature reaches the discrete temperature that corresponds to the chosen treatment option within about three seconds.

31. A method comprising:

choosing a treatment temperature using a selector on a skin heating apparatus, the treatment temperature being chosen from a plurality of specific temperatures in a range of approximately 46-62° C. based on one or more criteria selected from a specific skin condition, an area of the body to be treated, and a type of patient to be treated;

applying a heat application surface of the skin heating apparatus to a skin area having a specific skin problem, the heat application surface being heated to the treatment temperature by a heating element controlled by a control system; and introducing a therapeutically effective quantity of heat energy via the heat application surface, such that the skin area in contact with the heat application surface is raised to, and maintained at, the treatment temperature to treat the specific skin problem.

32. A method comprising:

applying a heat application surface of an apparatus to a skin area having a specific skin problem selected from a group consisting of acne, rash, eczema, psoriasis, hives, poison ivy, poison oak, dermatitis, herpes, and systemic skin itch, the apparatus comprising a heating element controlled by a control system that regulates the temperature of the heat application surface to a single preset temperature; and introducing a therapeutically effective quantity of heat energy via the heat application surface, such that the skin area in contact with the heat application surface is raised to, and maintained at, a temperature effective to treat the specific skin problem.

33. A method comprising:

applying a heat application surface of an apparatus to a skin area having a specific skin problem, the apparatus comprising a heating element controlled by a control system that regulates the temperature of the heat application surface to a single preset temperature;

introducing a therapeutically effective quantity of heat energy via the heat application surface, such that the skin area in contact with the heat application surface is raised to, and maintained at, a treatment temperature effective to treat the specific skin problem; and allowing the skin to cool down to a cooled temperature that is lower than the single preset temperature; and repeating the heating up and cooling down for one or more cycles to treat the skin condition.

* * * * *